(12) United States Patent
Lake et al.

(10) Patent No.: US 6,416,972 B1
(45) Date of Patent: *Jul. 9, 2002

(54) DNA ENCODING A PROSTAGLANDIN F2α RECEPTOR, A HOST CELL TRANSFORMED THEREWITH AND AN EXPRESSION PRODUCT THEREOF

(75) Inventors: Staffan Lake, Lidingö; Johan Stjernschantz, Uppsala, both of (SE)

(73) Assignee: Pharmacia & Upjohn Aktiebolag, Stockholm (SE)

( * ) Notice: Subject to any disclaimer, the term of this patent is extended or adjusted under 35 U.S.C. 154(b) by 0 days.
This patent is subject to a terminal disclaimer.

(21) Appl. No.: 08/880,865

(22) Filed: Jun. 23, 1997

Related U.S. Application Data

(63) Continuation of application No. 08/416,756, filed as application No. PCT/SE93/00789 on Oct. 1, 1993, now Pat. No. 5,750,369.

(30) Foreign Application Priority Data

Oct. 2, 1992 (SE) .............................................. 9202892

(51) Int. Cl.$^7$ ................................................ C12P 21/06
(52) U.S. Cl. ..................... 435/69.1; 536/23.5; 536/23.1; 536/24.31; 435/325; 435/320.1; 435/252.3; 435/254 N
(58) Field of Search .............................. 435/69.1, 320.1, 435/252.3, 254.11, 471, 71.1, 71.2; 536/23.5, 23.1, 24.31; 530/350

(56) References Cited

U.S. PATENT DOCUMENTS

| 5,869,281 A | 2/1999 | Abramovitz et al. | ....... 435/69.1 |

FOREIGN PATENT DOCUMENTS

| CA | 2064131 | 9/1992 |
| EP | 0 490 410 A1 | 6/1992 |
| WO | WO 95/00551 | 1/1995 |

OTHER PUBLICATIONS

Alm, A. and Villumsen, J., "PhXA34, a New Potent Ocular Hypotensive Drug," *Arch. Ophthalmol. 109:* 1564–1568 (1991).
Balapure, A.K. et al., "Multiple Classes of Prostaglandin $F_{2\alpha}$ Binding Sites in Subpopulations of Ovine Luteal Cells," *Biol. Reproduc. 41*:385–392 (1989).
Coleman, R.A. et al., "Prostanoids and their Receptors," *Comprehensive Medicinal Chemistry 3*:643–659 (1989).
Dohlman, H.G. et al., "A Family of Receptors Coupled to Guanine Nucleotide Regulatory Proteins," *Biochemistry 26(10)*:2657–2664 (1987).
Duncan, R.A. and Davis, J.S., "Prostaglandin $F_{2\alpha}$ Stimulates Inosito 1,4,5–Trisphosphate and Inositol 1,3,4,5–Tetrakisphosphate Formation in Bovine Luteal Cells," *Endocrinology 128(3)*:1519–1526 (1991).
Hirata, M. et al., "Cloning and expression of cDNA for a human thromboxane $A_2$ receptor," *Nature 346*:617–620 (1991).

Kozak, M., "Compilation and analysis of sequences upstream from the translational start site in eukaryotic mRNAs," *Nucl. Acids Res. 12(2)*:857–872 (1984).
Kyldén, U. and Hammarström, S., "Molecular Weight of Detergent–Solubilized Prostaglandin–$F_{2\alpha}$ Receptor from Bovine Corpora Lutea,"*Eur. J. Biochem. 109*:489–494 (1980).
Leung, P.C.K. et al., "Induction of Polyphosphoinositide Breakdown in Rat Corpus Luteum by Prostaglandin $F_{2\alpha}$," *Endocrinology 119(1)*:12–18 (1986).
Masu, Y. et al., "cDNA cloning of bovine sustance–K receptor through oocyte expression system," *Nature 329*:836–838 (1987).
Muallem, S. et al., "Classification of prostaglandin receptors based on coupling to signal transduction systems," *Biochem. J. 263*:769–774 (1989).
Namba, T. et al., "Mouse Thromboxane $A_2$ Receptor: cDNA Cloning, Expression and Northern Blot Analysis," *Biochem. Biophys. Res. Comm. 184(3)*:1197–1203 (May 1992).
Orlicky, D.J. et al., "Identification and Purification of a Bovine Corpora Luteal Membrane Glycoprotein with [$^3$H] Prostaglandin $F_{2A}$ Binding Properties," *Prostaglandins Leukotrienes and Essential Fatty Acids 41*:51–61 (1990).
Orlicky, D.J. et al., "Immunohistochemical Localization of $PGF_{2\alpha}$ Receptor in the Rat Ovary," *Prostaglandins Leukotrienes and Essential Fatty Acids 46*: 223–229 (Jul. 1992).
Sibley, D.R. et al., "Regulation of Transmembrane Signaling by Receptor Phosphorylation," *Cell 48*:913–922 (1987).
Strader, C.D. et al., "Structural basis of β–adrenergic receptor function," *FASEB J. 3*:1825–1832 (1989).
Sugimoto, Y. et al., "Cloning and Expression of a cDNA for Mouse Prostaglandin E Receptor $EP_3$ Subtype," *J. Biol. Chem. 267(10)*:6463–6466 (Apr. 1992).
Mikayama et al. Proc. Natl. Acad. Sci. USA, vol. 90, pp. 10056–10060. 1993.*
Voet et al. Biochemistry. John Wiley & Sons, Inc., pp. 126–128 and 228–234. 1990.*

* cited by examiner

*Primary Examiner*—Prema Mertz
(74) *Attorney, Agent, or Firm*—Birch, Stewart, Kolasch & Birch, LLP

(57) ABSTRACT

Molecular cloning and expression of a prostaglandin F2α receptor which is linked to the signal transduction pathways via guanine nucleotide binding regulatory (G) proteins and measured by, for example, cAMP, $IP_3$ or intracellular calcium. By constructing cell lines that express a prostaglandin F2α receptor, the affinities and efficacies of agonist and antagonist drugs with the receptor can be assessed. A recombinant DNA construct includes a vector and a DNA fragment encoding a prostaglandin F2α receptor. A host cell is transformed with a recombinant DNA construct, so that the DNA fragment is expressed and a prostaglandin F2α receptor is produced. Suitable host systems include eukaryotic and prokaryotic cells, especially mamalian cells such as rat or human. Additionally, for diagnostic purposes, antibodies to a prostaglandin F2α receptor can be prepared by producing all or a portion of the receptor protein and injecting these into various types of mammals. Using the resulting antibodies, expression of an F2α receptor cDNA, i.e. receptor protein in tissue and cells can be measured.

34 Claims, 8 Drawing Sheets

Fig. 1A

```
                                          TCCACAACGATGTCCATAAACAGTTCCAAG
                                       ----+----|----+----|----+----|--- 20
                                          AGGTGTTGCTACAGGTATTTGTCAAGGTTC
                                           -9
                                            S  T  T  M  S  I  N* S  S  K
                                           -3

CAGCCGGGGCTCCTCTGCAGCTCATCGCCCAACACGAGACTTGCCAGACGGAGAACCGG
---+----|----+----|----+----|----+----|----+----|----+----|--- 80
GTCGGCCCCGAGGAGACGTCGAGTAGCGGTTGTGCTCTGAACGGTCTGCCTCTTGGCC
 Q  P  A  S  S  A  A  G  L  I  A  N* T  T  C  Q  T  E  N  R
 8

CTTTCAGTGTTCTTTTCAATAATCTTCATGACGGTGGGATTGTATCTAACAGCCTGGCC
---+----|----+----|----+----|----+----|----+----|----+----|--- 140
GAAAGTCACAAGAAAAGTTATTAGAAGTACTGCCACCCTAACATAGATTGTCGGACCGG
 L  S  V  F  F  S  I  I  F  M  T  V  G  I  V  S  N  S  L  A
 28

ATTGCCATCCTCATGAAGGCATATCAGAGATTTAGACGAAGTCGAAGGCTTCTTTCCTG
---+----|----+----|----+----|----+----|----+----|----+----|--- 200
TAACGGTAGGAGTACTTCCGTATAGTCTCTAAATCTGCCTTCAGCTTCCGAAGAAAGGAC
 I  A  I  L  M  K  A  Y  Q  R  F  R  R  K  S  K  A  S  F  L
 48

CTCTTGGCTAGTGGCCTGGTGATCACAGACTTCTTCGGCCACCTCATCAACGGAGGGATA
---+----|----+----|----+----|----+----|----+----|----+----|--- 260
GAGAACCGATCACCGGACCACTAGTGTCTGAAGAAGCCGGTGGAGTAGTTGCCTCCCTAT
 L  L  A  S  G  L  V  I  T  D  F  F  G  H  L  I  N  G  G  I
 68
```

Fig. 1B

```
     GCTGTCTTCGTATACGCTTCTGATAAAGACTGGATCCGCTTCGATCAATCGAACATCCTG
     ---------+---------+---------+---------+---------+---------+  320
     CGACAGAAGCATATGCGAAGACTATTTCTGACCTAGGCGAAGCTAGTTAGCTTGTAGGAC
  88  A  V  F  V  Y  A  S  D  K  D  W  I  R  F  D  Q  S  N  I  L

TGCAGTGTTTTTGGGATCTCCATGGTGTTCTCTGGCTTGTGCCCACTTTTCCTGGGCAGT
     ---------+---------+---------+---------+---------+---------+  380
     ACGTCACAAAAACCCTAGAGGTACCACAAGAGACCGAACACGGGTGAAAAGGACCCGTCA
 108  C  S  V  F  G  I  S  M  V  F  S  G  L  C  P  L  F  L  G  S

ACGATGGCCATTGAGAGGTGCATCGGGTCACCAACCCTCTATTCCACTCTACAAAGATC
     ---------+---------+---------+---------+---------+---------+  440
     TGCTACCGGTAACTCTCCACGTAGCCCAGTGGTTGGGAGATAAGGTGAGATGTTTCTAG
 128  T  M  A  I  E  R  C  I  G  V  T  N  P  L  F  H  S  T  K  I

ACGTCTAAGCATGTGAAAATGATACTGAGCGGTGTGTGCATGTTTGCTGTCTTCGTGGCC
     ---------+---------+---------+---------+---------+---------+  500
     TGCAGATTCGTACACTTTTACTATGACTCGCCACACGTACAAACGACAGAAGCACCGG
 148  T  S  K  H  V  K  M  I  L  S  G  V  C  M  F  A  V  F  V  A

CTGTTGCCCATCCTTGGACACCGAGATTATCAAATCCAAGCATCCAGAACTTGGTGCTTC
     ---------+---------+---------+---------+---------+---------+  560
     GACAACGGGTAGGAACCTGTGGCTCTAATAGTTTAGGTTCGTAGGTCTTGAACCACGAAG
 168  L  L  P  I  L  G  H  R  D  Y  Q  I  Q  A  S  R  T  W  C  F
```

Fig. 1C

```
          TACAACACAGAGCACATCGAAGACTGGGAAGACAGGTTCTATCTCTTGTTCTTTTCTTCC
          ----------+---------+---------+---------+---------+---------+ 620
          ATGTTGTGTCTCGTGTAGCTTCTGACCCTTCTGTCCAAGATAGAAGAACAAGAAAAGAAGG
188       Y  N  T  E  H  I  E  D  W  E  D  R  F  Y  L  L  F  S  S

CTGGGACTCTTAGCTCTCTTGGCATTCTCATTCTCCGTGCAACGCCGTCACGGAGTCACACTT
          ----------+---------+---------+---------+---------+---------+ 680
          GACCCTGAGAATCGAGAACCGTAGAGTAAGAGCACGTTGCGGCAGTGCCCTCAGTGTGAA
208       L  G  L  L  A  L  G  I  S  F  S  C  N  A  V  T  G  V  T  L

TTGAGAGTGAAGTTTAGAAGTCAGCAGCACAGGCAGGTCTCACCACCTGGAGATG
          ----------+---------+---------+---------+---------+---------+ 740
          AACTCTCACTTCAAATCTTCAGTCGTCGTCCGTTCCGTCCAGAGTGGTGGACCTCTAC
228       L  R  V  K  F  R  S  Q  Q  H  R  Q  G  R  S  H  H  L  E  M

GTCATTCAGCTCCCTGGCCATAATGTGTCTCCCTGCCTGCTGGAGTCCCTTTCTGGTG
          ----------+---------+---------+---------+---------+---------+ 800
          CAGTAAGTCGAGGACCGGTATTACACAGAGGACGCAGACCTCAGGGAAAGACCAC
248       V  I  Q  L  L  A  I  M  C  V  S  C  V  C  W  S  P  F  L  V
```

Fig. 1D

```
      ACGATGGCCAACATTGCAATCAATGGAAATAATTCCCCAGTGACCTGTGAGACGACGCTC
      ----------+---------+---------+---------+---------+---------+  860
      TGCTACCGGTTGTAACGTTAGTTACCTTTATTAAGGGGTCACTGGACACTCTGCTGCGAG
268   T  M  A  N  I  A  I  N  G  N* N  S  P  V  T  C  E  T  T  L

TTTGCTCTCCGAATGGCAACCTGGAACCAGATATTAGACCCCTGGGTCTACATTCTGCTA
      ----------+---------+---------+---------+---------+---------+  920
      AAACGAGAGGCTTACCGTTGGACCTTGGTCTATAATCTGGGACCCAGATGTAAGACGAT
288   F  A  L  R  M  A  T  W  N  Q  I  L  D  P  W  V  Y  I  L  L

CGGAAAGGCTGTCCTTAGGAACCTGTACAAGCTTGCCAGTCGCTGCTGTGGAGTGAACATC
      ----------+---------+---------+---------+---------+---------+  980
      GCCTTCCGACAGGAATCCTTGGACATGTTCGAACGGTCAGCGACGACACCTCACTTGTAG
308   R  K  A  V  L  R  N  L  Y  K  L  A  S  R  C  C  G  V  N  I

ATCAGCTTGCACATCTGGGAACTCAGCTCCATCAAGAATTCCTTAAAGGTTGCTGCTATC
      ----------+---------+---------+---------+---------+---------+ 1040
      TAGTCGAACGTGTAGACCCTTGAGTCGAGGTAGTTCTTAAGGAATTTCCAACGACGATAG
328   I  S  L  H  I  W  E  L  S  S  I  K  N  S  L  K  V  A  A  I

TCTGAGTCACCGGCTGCAGAGAAGGAGAATCAGCAAGCATCTAGTGAGGCTGGACTGTAA
      ----------+---------+---------+---------+---------+---------+ 1100
      AGACTCAGTGGCCGACGTCTCTTCCTCTTAGTCGTTCGTAGATCACTCCGACCTGACATT
348   S  E  S  P  A  A  E  K  E  N  Q  Q  A  S  S  E  A  G  L  *
```

```
GTCAATGCA
--------- 1109
CAGTTACGT
 V  N  A
```

```
Name: RatFP2a  =3
Name: HumTXA2  =2
Name: MusEP3   =1

1                                                        50
  3   .MSINSSKQP ASSAAGLIAN TTCQTENRLS VFFSIIFMTV GIVSNSLAIA
  2   .MWPNGS..S LGPCFRPTNI TLEERRLIAS PWFAASFCVV GLASNLLALS
  1   MASMWAPEHS AE.AHSNLSS TTDDCGSV.S VAFPITMMVT GFVGNALAML
                                       --------tm1----------

51                                                      100
  3   ILMKAYQRFR RKSKASFLLL ASGLVITDFF GHLINGGIAV FVYASDKDWI
  2   VLAGA.RQGG SHTRSSFLTF LCGLVLTDFL GLLVTGTIVV SQHAALFEWH
  1   LVSRSYRRRE SKRKKSFLLC IGWLALTDLV GQLLTSPVVI LVYLSQRRWE
                                       ---------tm2---------

101                                                     150
  3   RFDQSNILCS VFGISMVFSG LCPLFLGSTM AIERCIGVTN PLFHSTKITS
  2   AVDPGCRLCR FMGVVMIFFG LSPLLLGAAM ASERYLGITR PFSRPAVASQ
  1   QLDPSGRLCT FFGLTMTVFG LSSLLVASAM AVERALAIRA PHW...YASH
                         -----------tm3-----------
```

Fig. 2B

```
      151                                                            200
3   KHVK..MILS GVCMFAVFVA LLPILGHRDY QIQASRTWCF YNTEHIE....
2   RRAWATVGL. .VWAAALALG LLPLLGVGRY TVQYPGSWCF LTLGA......
1   MKTRATPVLL GVWLSVLAFA LLPVLGVGRY SVQWPGTWCF ISTGPAGNET
                      -----tm4------

201                                                            250
3   ....DWEDRF YLLFFSSLGL LALGISFSCN AVTGVTLLRV KFRSQQHRQG
2   ....ESGDVA FGLLFSMLGG LSVGLSFLLN TVSVATLCHV .YHGQEAAQQ
1   DPAREPGSVA FASAFACLGL LALVVTFACN LATIKALVSR .CRAKAAVSQ
                            -----tm5-----

251                                                            300
3   RSHH......L EMVIQLLAIM CVSCVCWSPF LVTMANIAIN GN........
2   RPRDSE...V EMMAQLLGIM VVASVCWLPL LVFIAQTVLR NPPAMSPAGQ
1   SSAQWGRITT ETAIQLMGIM CVLSVCWSPL LIMMLKMIFN QMSVEQCKTQ
                                      -----tm6-----

301                                                            350
3   NSPVT.CETT LFALRMATWN QILDPWVYIL LRKAVLRNLY KLASRCCGVN
2   LSRTTE.KEL LIYLRVATWN QILDPWVYIL FRRAVLRRL. ..........
1   MGKEKECNSF LIAVRLASLN QILDPWVYLL LRKILLRKFC ..........
                                    -----tm7-----
```

Fig. 2C

```
    351                                                      391
1   IISLHIWELS SIKNSLKVAA ISESPAAEKE NQQASSEAGL *
2   ....QPRLST RPRSLSLQPQ LTQRSGLQ*. .......... .
3   ....QIRDHT NYASSSTSLP CPGSSALMWS DQLER*.... .
```

DNA ENCODING A PROSTAGLANDIN F2α RECEPTOR, A HOST CELL TRANSFORMED THEREWITH AND AN EXPRESSION PRODUCT THEREOF

This application is a continuation of application Ser. No. 08/416,756, now U.S. Pat. No. 5,750,369 which is the U.S. National Phase of PCT/SE93/00789, international filing date Oct. 1, 1993.

BACKGROUND OF THE INVENTION

1. Technical Field

The present invention relates, in general, to the molecular cloning and expression of a receptor protein, and, in particular, to a prostaglandin F2α receptor and fragments thereof linked to the activation of second messengers as measured, for example, by cAMP, $IP_3$ or intracellular calcium. The invention further relates to a DNA sequence encoding a prostaglandin F2α receptor, to a recombinant DNA molecule that includes such a DNA sequence and to cells transformed therewith. The invention also relates to antibodies directed against the F2α receptor and to a method of detecting an F2α receptor with the antibody. The invention further relates to a method of detecting the presence of an F2α receptor encoding a DNA fragment in a sample, the use of transformed cells for screening drugs, as well as to drugs prepared using such a screening method.

2. Background Information

Prostaglandin F2α receptors belong to a large class of hormone receptors which are linked to their signal transduction pathways via guanine nucleotide binding regulatory (G) proteins. Such receptors are amongst the most intensively studied receptor systems. Prostaglandin receptors have been classically defined as being linked to the stimulation of second messengers and measured by cyclic AMP (cAMP), inositol 3-phosphate ($IP_3$) or intracellular calcium and are coupled with a G regulatory protein (Muallem, Biochem. J. 263: 769–774 (1989)). In contrast, activation of prostaglandin receptors may result in various responses, including inhibition of adenylyl cyclase activity, inhibition of phosphatidylinositol turnover and inhibition of $Ca^{2+}$ mobilization (Muallem, Biochem. J. 263: 769–774 (1989), and Duncan, Endocrinology 128: 1519–1526 (1991)). Evidence has also accumulated suggesting heterogeneity in the category of receptors (Balapure, Biol. Reprod. 41: 385–392 (1989)).

Two prostaglandin receptors have previously been cloned, viz. the human and mouse thromboxane A2 receptor and the mouse prostaglandin $E_3$ receptor (Hirata, Nature 349: 617–620 (1991); Namba, BBRC 184: 1197–1203 (1992); and Sugimoto, J. Biol. Chem. 267: 6463–6466 (1992), respectively).

Prostaglandin F2α receptors are extremely important from a clinical therapeutic viewpoint. Drugs which activate (agonists) these receptors may be used to treat glaucoma (Alm, Arch. Ophthalmol. 109:1564–1568 (1991)), whereas drugs which block (antagonists) prostaglandin F2α receptors may be used therapeutically to treat pathological conditions, e.g. in the lungs and uterus. It may be of pharmaceutical value to be able to titer endogenous prostaglandin F2α with a solubilized receptor as well as to use an immobilized receptor in the purification of a ligand and its analogs. Despite their clinical utility, one problem with the prostaglandin F2α agonist and putatively antagonist drugs currently available, is that they have many side effects, like many other drugs which work through interaction with receptors. These side effects are predominantly due to a lack of receptor specificity. That is, the drug in use interacts not only with prostaglandin F2α receptors but with other receptors as well, see e.g. Muallem, Biochem. J. 263;769–774 (1989).

A major goal of clinical pharmacology and the pharmaceutical industry is the development of more selective drugs with greater efficacy than those currently in use. Impediments to this process are the low abundance of prostaglandin F2α receptor protein available to study in eye tissue and the lack of suitable homogeneous model systems of the receptors with which to screen drugs against.

SUMMARY OF THE INVENTION

The present invention seeks to provide a solution to this problem by a novel approach which comprises cloning cDNAs encoding prostaglandin F2α receptors, constructing eukaryotic expression vectors containing these cDNAs, and creating a series of stably transfected mammalian cell lines or prokaryotic cells which express functional prostaglandin F2α receptors in high abundance. These cell lines, which would express a homogeneous population of prostaglandin F2α receptors, can be used by the pharmaceutical industry or others to screen drugs and study the prostaglandin F2α receptors using a variety of biochemical, physiological and pharmacological techniques.

To accomplish this goal, we have isolated a cDNA encoding a rat prostaglandin F2α receptor subtype linked to the activation of second messengers as measured by e.g. cAMP, $IP_3$ or intracellular calcium. This cDNA encoding an F2α receptor is inserted into different eukaryotic and prokaryotic expression vectors and used in the construction of various mammalian cell lines expressing this functional protein. Resulting F2α receptor-expressing cell lines can be used to investigate the affinities and efficacies of agonist and antagonist drugs with an F2α receptor using various techniques, such as radioligand binding and second messenger assays.

One aspect of the present invention therefore relates to an F2α receptor that is linked to the stimulation of second messengers, such as cAMP, $IP_3$ or intracellular calcium, and that couples with guanine nucleotide binding regulatory (G) proteins, when present.

Another aspect of the present invention relates to a DNA fragment encoding the above described prostaglandin F2α receptor.

A further aspect of the present invention relates to a recombinant DNA construct or molecule comprising a vector and the above-described DNA fragment.

Yet another aspect of the present invention relates to a host cell transformed with the above described recombinant DNA construct.

In another aspect, the present invention relates to a process of producing the above-described prostaglandin F2α receptor. The method comprises culturing the above-mentioned host cell under conditions such that the F2α receptor encoding DNA fragment is expressed and a prostaglandin F2α receptor is produced.

Still another aspect of the invention relates to an antibody directed against the F2α receptor.

Another aspect of the invention relates to a method of detecting the presence of an F2α receptor in a sample by contacting the sample with such an antibody.

Still another aspect of the invention relates to a method of detecting the presence in a sample of a DNA fragment encoding an F2α receptor by contacting the sample with a DNA probe comprising a DNA fragment encoding an F2α receptor protein or polypeptide to hybridize the DNA fragment thereto.

Yet another aspect of the invention relates to a method of screening drugs for F2α receptor activating or blocking activity by contacting the above-mentioned transformed host cell with the drugs.

Another aspect of the invention relates to a method of preparing a drug, which method includes screening drug candidates for F2α receptor activating or blocking activity.

A further aspect of the invention relates to a drug, the preparation of which included screening drug candidates for F2α receptor activating or blocking activity.

BRIEF DESCRIPTION OF THE DRAWINGS

FIGS. 1A, 1B, 1C, 1D, 1E, 2A, 2B, and 2C show the sequence of a rat prostaglandin F2α receptor (SEQ ID NOS:1 and 2) and comparison with the sequences of other G protein-coupled receptors (SEQ ID NOS:3–5).

FIGS. 1A, 1B, 1C, 1D and 1E show the nucleotide sequence of an F2α receptor (SEQ ID NO:1) along with the deduced amino acid sequence of the longest open reading frame (SEQ ID NO:2). The nucleotide sequence is numbered from the putative initiator methionine and indicated at the left of each line while the amino acid numbers are indicated at the right of each line. The postulated N-linked glycosylation sites are indicated by an asterisk. The potential site for phosphorylation by the cAMP-dependent protein kinase is underlined.

FIGS. 2A, 2B, and 2C show a comparison of a prostaglandin F2α receptor amino acid sequence with that of other known prostaglandin receptors. Amino acid sequences of the human thromboxane $A_2$ receptor (2) (SEQ ID NO:4) and the mouse prostaglandin $E_3$ receptor (1) (SEQ ID NO:3) were aligned to optimize the homology with a rat prostaglandin F2α receptor sequence (3) (SEQ ID NO:5). Amino acid identities between the F2α and the two other prostaglandin receptors are indicated with bold type. The putative transmembrane (TM) regions are indicated by the dashed lines.

DETAILED DESCRIPTION OF THE INVENTION

The present invention relates to a prostaglandin F2α receptor that is linked to the activation of second messengers, for example, as measured by cAMP, $IP_3$ or intracellular calcium, and that is coupled with the guanine nucleotide binding regulatory (G) protein, when present. The invention further relates to DNA sequences (fragments) encoding all, or parts of an F2α receptor protein or a sequence that hybridizes therewith. The invention also relates to a recombinant construct containing such DNA sequences, to cells transformed therewith, and to methods of expressing the receptor gene. Also, the invention relates to an antibody to the F2α receptor and the use of the antibody for detecting the presence of an F2α receptor in the sample. The invention further relates to a method for detecting the presence in a sample of a DNA fragment encoding an F2α receptor. The invention also relates to a method for screening drugs by means of the transformed cells. Furthermore, the invention relates to a method of preparing drugs, which method includes such a screening procedure, as well as to drugs prepared by the method.

The F2α receptor protein or polypeptide of the present invention is one of a large class of receptors which are linked to their signal transduction via guanine nucleotide binding regulatory proteins. Specifically, an F2α receptor of the invention is linked to the activation of second messengers as measured by, for example, cAMP, $IP_3$ or intracellular calcium, and couples with the G regulatory protein, when present (e.g. prokaryotic systems lack G regulatory proteins).

Figure 1E:
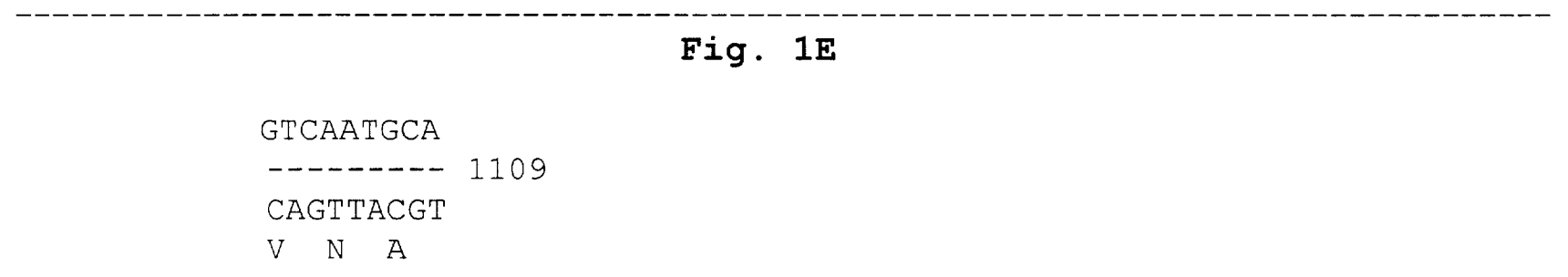

The term "F2α receptor" as used herein in the context of the present invention is to be understood in a broad sense. Thus, an F2α receptor can have the complete sequence given in FIGS. 1A through 1E (SEQ ID NO:2), or can have the amino acid sequence of a molecule having substantially the same second messenger properties as measured by e.g. cAMP, $IP_3$ or intracellular calcium, pharmacological properties, and G regulatory protein coupling properties of the molecule corresponding to FIGS. 1A through 1E (SEQ ID NO:2) (for example, allelic variations of the F2α receptor protein). Alternatively, an F2α receptor protein (or polypeptide) of the invention can have an amino acid sequence corresponding to any active portion or parts of a protein depicted in FIGS. 1A through 1E (SEQ ID NO:2) (or allelic variations thereof). As an example, an F2α receptor protein (or polypeptide) can have an amino acid sequence corresponding to an epitope of the FIGS. 1A through 1E sequence (SEQ ID NO:2) (or an allelic variation thereof).

The F2α receptor protein or polypeptide can be present in a substantially pure form, that is, in a form substantially free of proteins and nucleic acids with which it is normally associated. An F2α receptor protein can be purified using protocols known in the art. An F2α receptor protein can also be used as an antigen, in protocols known in the art, to produce antibodies thereto, both monoclonal and polyclonal.

As indicated above, the present invention also relates to DNA sequences (including cDNA sequences) that encode the entire amino acid sequence given in FIGS. 1A through 1E (SEQ ID NO:2) (the specific cDNA sequence given in FIGS. 1A through 1E being only one example), or any portion thereof. The DNA sequences to which the invention relates also include those encoding proteins (or polypeptides) having substantially the same second messengers properties as measured by, for example, cAMP, $IP_3$ or intracellular calcium, pharmacological properties, and G regulatory protein coupling properties of an F2α receptor (for example, allelic forms of the sequence of FIGS. 1A through 1E) (SEQ ID NO:2).

Further, the present invention relates to a recombinant DNA construct that includes a vector and a DNA sequence as described above (advantageously, a DNA sequence encoding the receptor shown in FIGS. 1A through 1E or a receptor having the same second messenger properties as measured by, for example, cAMP, $IP_3$ or intracellular calcium, pharmacological properties, and G protein coupling properties of that protein).

The vector can take the form of a virus or a plasmid vector (for example, lambda ZAP II). The DNA sequence can be present in the vector operably linked to regulatory elements, including, for example, a promoter. The recombinant construct can be suitable for transforming prokaryotic or eukaryotic cells, or advantageously, mammalian cells.

The present invention also relates to a host cell transformed with the above described recombinant construct. The host can be prokaryotic (for example, bacterial), lower eukaryotic (i.e., fungal, including yeast) or higher eukaryotic (i.e., all mammalian, including but not limited to rat and human). For instance, stable transformations are accomplished into Chinese hamster ovary cells (CHO-cells). Transformation can be effected using methods known in the art. The transformed host cells can be used as a source for the DNA sequence described above (which sequence constitutes part of the recombinant construct). When the recombinant receptor takes the form of an expression system, the transformed cells can be used as a source for the above-described receptor.

The presence of an F2α receptor protein can be detected in a sample (for instance, tissue from a human or other mammal, or a cell culture) by contacting the sample with an antibody to the receptor. The detection of the presence or absence of a complex formed between the receptor and the antibody may be accomplished by methods well known in the art. The presence of a DNA segment encoding an F2α receptor protein can be detected in a sample (for instance, tissue from a human or other mammal, or a cell culture) by contacting the sample with a DNA probe that is comprised of the DNA segment or fragments thereof. Using methods well known in the art and under conditions such that hybridization will occur, a complex can be formed between the probe and the DNA segment from the sample. Detection of the presence or absence of the complex may be accomplished by methods well known in the art.

A prostaglandin F2α receptor protein and nucleic acid sequences of the present invention can be used both in a research setting (for example, to facilitate an under-standing of receptor protein mechanisms) and in a clinical setting (for example, to use as a model system of the receptor with which to screen agonist and antagonist drugs against). For instance, therapeutic drugs designed to interact with prostaglandin F2α receptors often have side effects, due to lack of receptor specificity. A cell line expressing an F2α receptor can be used to investigate the affinities and efficacies of agonist and antagonist drugs with an F2α receptor using various techniques, such as radioligand binding and second messenger assays. The activity of the drug-treated cell can be compared to a control cell to evaluate the activation or blocking of an F2α receptor.

For diagnostic purposes, expression of an F2α receptor cDNA in cells can be measured using known methods. To accomplish this, antibodies to an F2α receptor (prepared by producing all or portions of an F2α receptor protein and injecting these into various types of animals, e,g., rabbits, sheep, goats, or mice) can be used.

The invention is described in further detail below and in the following non-limiting Example with regard to the isolation and characterization of cDNA clones for an F2α receptor.

Isolation and Characterization of cDNA Clones for a Prostaglandin F2α Receptor (i) Cloning and Sequencing Analyses of Prostaglandin F2α Receptor cDNA:

In order to clone a prostaglandin F2α receptor, hereinafter for brevity often called FP-receptor, linked to second messenger activation as measured by e.g. cAMP, IP$_3$ or intracellular calcium, the PCR method was used to selectively amplify cDNA sequences from mRNA purified from rat corpora lutea. Ovine and bovine corpora lutea have previously been shown to express this receptor subtype (Balapure, Biol. of Reproduction 41: 385–392 (1989) and Orlicky, Prostaglandins Leukotrines and Essential Fatty Acids 41: 51–61 (1990)). A commercial cDNA library was used to obtain cDNA from rat corpora lutea. PCR amplification was performed with a pair of highly degenerate primers (SEQ ID NOS:6 and 7) derived from the second and seventh and third and sixth transmembrane regions of previously cloned seven transmembrane receptor superfamily members. This process resulted in the amplification of several cDNA fragments.

These fragments were preliminarily characterized by DNA sequence analysis. One of these fragments was found to exhibit considerable sequence homology to related previously cloned G protein-coupled receptors and was subsequently used to screen the rat corpora lutea cDNA library in order to isolate a full-length clone. Twenty-four cDNA clones with insert sizes ranging from about 1.7 to 3.3 kb were isolated, all of which strongly hybridized with the $^{32}$P-labelled PCR probe on Southern analysis. One of these clones with an insert of about 3 kb was sequenced and found to exhibit more than 55% amino acid sequence homology to related receptors in the coding regions of the sequence. The homology is about the same in all combinations, in spite of the different receptors and also the in one case different species, human vs. rat. The nucleotide and deduced amino acid sequences for clone FP are shown in FIGS. 1A through 1E (SEQ ID NOs:1 and 2). The longest open reading frame in this cDNA codes for a 366 residue protein with a theoretical molecular weight of 40.65 kDa.

Although there are neighbouring sequences with ATG in this reading frame similar to Kozak's consensus initiation sequence (Kozak, Nucleic Acids Res., 12:857–872 (1984)), the Met codon at position 1 actually provides the most probable site (FIGS. 1A through 1E (SEQ ID NO:1)).

Hydrophobicity analysis of the translated protein reveals seven clusters of about 20–25 hydrophobic residues, predicted to represent transmembrane-spanning domains, connected by three extracellular and three intracellular loops. This pattern is similar to that observed for other cloned G protein-coupled receptors where the NH$_2$ terminus is proposed to be extra-cellular and the COOH terminus projects into the cytoplasm (Dohlman, Biochemistry, 26:2657–2664 (1987)). The NH$_2$ terminus contains two consensus site for N-linked glycosylation while the predicted third cytoplasmic loop exhibits one. Consensus recognition sites for phosphorylation by the cAMP-dependent protein kinase are found in the cytoplasmic loops and the carboxy tail. In addition, the long COOH terminus contains several serine residues possibly representing additional sites for regulatory phosphorylation. These phosphorylations are proposed for the regulation of transmembrane signaling and desensitization of the receptor (Sibley, Cell. 48:913–922 (1987)).

(ii) Characterization of the Amino Acid Sequences for a Prostaglandin F2α Receptor Clone:

A comparison of the deduced amino acid sequence for the cDNA clones with the sequences of various prostaglandin receptors is shown in FIGS. 2A through 2C (SEQ ID NOS:3–5). As can be seen, the regions of highest identity appear to occur within the predicted transmembrane spanning domains. Within these regions, the FP receptor protein exhibits the highest sequence homologies with the rat prostaglandin E3 and thromboxane A2 receptor, mouse and human. The NH$_2$ and COOH termini and the extracellular and intracellular loops are significantly more divergent among these receptors. It is interesting to note that within the third putative transmembrane domain of FP, there is no conserved aspartate residue which is common to all biogenic amine receptors that have been sequenced thus far (Strader, FASEB J., 3: 1825–1832 (1989)). Moreover, the fifth transmembrane spanning domain of FP also contains two serine residues which are conserved among catecholamine receptors and are critical for the recognition of agonist ligands possessing a catechol group (Strader, FASEB J., 3: 1825–1832 (1989)).

Furthermore, with primers (SEQ ID NOS:8 and 9) derived from the sequence encoding the F2α receptor and using PCR in cDNA libraries from human tissue expected to express the F2α receptor, fragments of the correct size were found, showing between them identical restriction fragments. The tissues were e.g the eye, ovary, uterus and kidney.

These observations suggest that the F2α receptor cDNA clone of the present invention encodes a receptor for an endogenous prostaglandin ligand.

EXAMPLE

Isolation and Characterization of cDNA Clones for a New G Protein Coupled Receptor In order to clone an FP-receptor, the polymerase chain reaction (PCR) method was used to amplify cDNA sequences from Rat corpora lutea cDNA library in the lambda ZAP$^C$II vector, (stratagene, Catalogue No. 936504). $1 \times 10^6$ pfu of the library were amplified and lambda DNA was prepared as described in Current' Protocols in Molecular Biology (1990) 1.13.1–1.13.3. 50 ng of the lambda DNA were submitted to 45 cycles of PCR amplification in a total reaction volume of 25 µl with 1 µM each of the two primers:

TM206: 5' ATI I(CT) (CG) (TA)I(TC) (TC)TG GCI ITI ICC GAT 3' (SEQ ID NO:6) and

TM710: 5' C(GT)(AG) AAI AGI AT(AG) TAI ACC CAI GGG TC 3' (SEQ ID NO:7);

and 200 µM dNTPs and 2 u of Taq DNA polymerase (Perkin Elmer-Cetus, U.S.A.). The timing used was 45 seconds (in the first cycle 3 minutes) at 95 degrees Celsius, 3 minutes at 50 degrees Celsius and 3 minutes at 72 degrees Celsius. The 72 degrees Celsius step was extended with 6 seconds for each cycle. The reaction products were purified by electrophoresis in 1% LMP agarose (BioRad Laboratories, Richmond, Calif., U.S.A., Catalogue No. 162-0020). Individual bands were excised from the gel and were submitted to 20 cycles of PCR-amplification in a total reaction volume of 20 µl with 100 µM of each of the same two primers as above, i.e.:

TM206: 5' ATI I(CT) (CG) (TA)I(TC) (TC)TG GCI ITI ICC GAT 3' (SEQ ID NO:6) and

TM710: 5' C(GT)(AG) AAI AGI AT(AG) TAI ACC CAI GGG TC 3' (SEQ ID NO:7);

and 200 µM of dNTPs and 2,5 u of Taq DNA polymerase. The timing used was identical to the timing described above.

The reaction products were ligated into the vector PCR1000 according to the instructions of the TA Cloning Kit (Invitrogen Corporation, U.S.A., Catalogue no. K2000-1). The obtained plasmid was called pKGE858. Mini preparation of plasmid DNA was done with a Qiagene-tip 100 kit (Diagene-GmbH, Germany). Insert sequencing was performed according to methods well known in the art. Thus, the cDNA inserts were sequenced with primers homologous to regions on the M13 multiple cloning site. To reveal the whole cDNA sequences, a gene walking strategy was used. All sequence analyses were performed on an Applied Biosystem Model 373A DNA sequencing system (Applied Biosystems Inc., U.S.A.) according to Applied Biosystems' protocol for their Taq Dye Dioxy Terminator cycle sequencing kit. The generated primary data were processed on a VAX computer using the sequence analysis programs from Genetics Computer Group Inc., Madison, USA (Devereux, Nucleic Acids Research 12 (1): 387[\N]395 (1984)). One of the inserts was found to exhibit a sequence homology to related receptors (the human thromboxane A2 receptor and later on also to other cloned prostaglandin receptors; Hirata, Nature 349: 617–620 (1991), Sugimoto, J. Biol. Chem. 267: 6463–6466 (1992), and Namba BBRC 184: 1197–1203 (1992)). This insert was subsequently used as a probe to screen the rat Corpora lutea cDNA library to isolate a full-length clone. $1 \times 10^6$ recombinants from the rat Corpora lutea cDNA library, constructed in the Lambda ZAP II vector, were screened with the insert described above. The probe consisting of the NotI/HindIII 600 bp fragment of the plasmid pKGE858 obtained above was labelled with Amershams Megaprime DNA labelling system (Amersham, England, RPN1607). Duplicate nitrocellulose filters (Hybond-N, (Amersham, England) were hybridized in 10% (w/v) dextran sulfate, 1% sodium dodecyl sulfate, 1M sodium chloride and 100 µg/ml sonicated salmon sperm DNA (Boehringer Mannheim, Germany) with the probe described above for 16 h at 65 degrees Celsius. High stringency washing of the filters was performed with 2×SSC and 1% sodium dodecyl sulfate at 65 degrees Celsius for 30 minutes. Positively hybridizing phage clones were further purified by rescreening using the same probe as in the initial screening. 25 positively hybridizing purified phage clones were expanded in *E. coli* XL1-Blue (Stratagene, U.S.A.), and the resulting phage stocks used to prepare cDNA-containing pBluescript plasmids by phagemid excision using helper phage R408 according to the Stratagene protocol. Plasmid DNA was prepared with Qiagene-tip 100 (Diagene GmbH, Germany) and further analyzed by restriction analysis. The four plasmids with the longest inserts were analyzed by DNA sequencing methods well known in the art. The DNA sequence of one of these inserts is shown in FIGS. 1A through 1E.

To detect the F2α receptor in tissues expected to express the same, primers derived from the sequence encoding the F2x receptor in transmembrane (TM) regions VI and VII were used. The primer sequence in TM VI was:

5'-CCAGCTTCTGGGTATAATGTGTGT-3' (SEQ ID NO:8), and the primer sequence in TM VII was:

5'-AGCAGSATATARGCCCAGGGGTCCAAGATCT-GGTTCCRGGWTGCCATKCG -3' (SEQ ID NO:9).

The amplified product had a size of 173 bp. The PCR reactions were performed as above. By cutting the fragment with the restriction enzyme HaeIII, which is unique in the human fragment, two bands were obtained with the sizes 100 and 73 bp, respectively. Fragments from the cDNA libraries all showed these characteristics.

The entire contents of all references cited herein above are incorporated by reference.

While the foregoing invention has been described in some detail for purposes of clarity and understanding, it will be clear to one skilled in the art from a reading of this disclosure that various changes in form and detail can be made without departing from the true scope of the invention.

What is claimed is:

1. A purified nucleic acid comprising a nucleotide sequence that hybridizes to a sequence that is complementary to the sequence set forth in base numbers. 10 to 1107 of SEQ ID NO: 1 and remains hybridized to said sequence that is complementary when subjected to a 2×SSC and 1% sodium dodecyl sulfate wash at 65° C. for 30 min.

2. A method for making a recombinant vector comprising inserting the purified of claim 1 into a vector.

3. The recombinant vector obtained by the method of claim 2.

4. A method for making a recombinant host cell comprising transforming or transfecting a host cell with the recombinant vector of claim 3.

5. The method of claim 4, wherein said host cell is a prokaryotic cell.

6. The method of claim 4, wherein said host cell is a eukaryotic cell.

7. The host cell obtained by the method of claim 4.

8. The method of claim 2, wherein said nucleotide sequence encodes the amino acid sequence of amino acids 1 to 366 of SEQ ID No. 2.

9. The method of claim 8, wherein said nucleotide sequence is nucleotide 10 to 1107 SEQ ID No. 1.

10. The recombinant vector obtained by the method of claim 9.

11. A method for making a recombinant host cell comprising transforming or transfecting a host cell with the recombinant vector of claim 10.

12. The method of claim 11, wherein said host cell is a prokaryotic cell.

13. The method of claim 11, wherein said host cell is a eukaryotic cell.

14. The host cell obtained by the method of claim 11.

15. The recombinant vector obtained by the method of claim 8.

16. A method for making a recombinant host cell comprising transforming or transfecting a host cell with the recombinant vector of claim 15.

17. The method of claim 16, wherein said host cell is a prokaryotic cell.

18. The method of claim 16, wherein said host cell is a eukaryotic cell.

19. The host cell obtained by the method of claim 16.

20. A host cell transformed or transfected with a nucleic acid that comprises a nucleotide sequence that hybridizes to a sequence that is complementary to the sequence set forth in base numbers. 10 to 1107 of SEQ ID NO: 1 and remains hybridized to said sequence that is complementary when subjected to a 2×SSC and 1% sodium dodecyl sulfate wash at 65° C. for 30 min.

21. The host cell according to claim 20, wherein said cell is a eukaryotic host cell.

22. The host cell according to claim 20, wherein said cell is a prokaryotic host cell.

23. A vector comprising a nucleotide sequence that hybridizes to a sequence that is complementary to the sequence set forth in base numbers. 10 to 1107 of SEQ ID NO: 1 and remains hybridized to said sequence that is complementary when subjected to a 2×SSC and 1% sodium dodecyl sulfate wash at 65° C. for 30 min.

24. The vector according to claim 23, wherein said vector is a eukaryotic expression vector.

25. The vector according to claim 23, wherein said vector is a prokaryotic expression vector.

26. A host cell transformed or transfected with the vector according to claim 24 or 25.

27. The host cell according to claim 26, wherein said host cell is a eukaryotic host cell.

28. The host cell according to claim 26, wherein said host cell is a prokaryotic host cell.

29. A purified nucleic acid comprising at least 24 contiguous nucleotides of SEQ ID NO:1.

30. A purified nucleic acid comprising a nucleotide sequence encoding a prostaglandin F2 α receptor,
    wherein said nucleotide sequence is base numbers 10 to 1107 of SEQ ID NO:1, and
    wherein said prostaglandin F2 α receptor that is encoded by said nucleotide sequence binds prostaglandin F2 α when said prostaglandin F2 α receptor is expressed in a host cell transformed or transfected with said nucleotide.

31. The nucleic acid according to claim 77, wherein said nucleotide sequence encodes the amino acid sequence of amino acids 1 to 366 of SEQ ID:2.

32. A host cell transformed or transfected with a nucleic acid that comprises a nucleotide sequence encoding a prostaglandin F2 α receptor, wherein said nucleotide sequence is base numbers 10 to 1107 of SEQ ID NO:1, and wherein said prostaglandin F2 α receptor that is encoded by said nucleotide sequence binds prostaglandin F2 α when said prostaglandin F2 α receptor is expressed in said host cell.

33. A vector comprising the a nucleic acid comprising a nucleotide sequence encoding a prostaglandin F2 α receptor, wherein said nucleotide sequence is base numbers 10 to 1107 of SEQ ID NO:1, and wherein said prostaglandin F2 α receptor that is encoded by said nucleotide sequence binds prostaglandin F2 α when said prostaglandin F2 α receptor is expressed in a host cell transformed or transfected with said nucleotide.

34. A purified nucleic acid comprising a nucleotide sequence that hybridizes to a sequence that is complementary to at least 24 contiguous nucleotides of SEQ ID NO:1 and remains hybridized to said sequence that is complementary when subjected to a 2X SSC and 1% sodium dodecyl sulfate wash at 65° C for 30 min.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1119 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..1107

(ix) FEATURE:
      (A) NAME/KEY: mat_peptide
      (B) LOCATION: 10..1107

(xi) SEQUENCE DESCRIPTION: SEQ ID NO:1:

```
TCC ACA ACG ATG TCC ATA AAC AGT TCC AAG CAG CCG GCG TCC TCT GCA      48
Ser Thr Thr Met Ser Ile Asn Ser Ser Lys Gln Pro Ala Ser Ser Ala
 -3           1               5                  10

GCT GGA CTC ATC GCC AAC ACG ACT TGC CAG ACG GAG AAC CGG CTT TCA      96
Ala Gly Leu Ile Ala Asn Thr Thr Cys Gln Thr Glu Asn Arg Leu Ser
         15                  20                  25

GTG TTC TTT TCA ATA ATC TTC ATG ACG GTG GGG ATT GTA TCT AAC AGC     144
Val Phe Phe Ser Ile Ile Phe Met Thr Val Gly Ile Val Ser Asn Ser
 30                  35                  40                  45

CTG GCC ATT GCC ATC CTC ATG AAG GCA TAT CAG AGA TTT AGA CGG AAG     192
Leu Ala Ile Ala Ile Leu Met Lys Ala Tyr Gln Arg Phe Arg Arg Lys
                 50                  55                  60

TCG AAG GCT TCT TTC CTG CTC TTG GCT AGT GGC CTG GTG ATC ACA GAC     240
Ser Lys Ala Ser Phe Leu Leu Leu Ala Ser Gly Leu Val Ile Thr Asp
                 65                  70                  75

TTC TTC GGC CAC CTC ATC AAC GGA GGG ATA GCT GTC TTC GTA TAC GCT     288
Phe Phe Gly His Leu Ile Asn Gly Gly Ile Ala Val Phe Val Tyr Ala
             80                  85                  90

TCT GAT AAA GAC TGG ATC CGC TTC GAT CAA TCG AAC ATC CTG TGC AGT     336
Ser Asp Lys Asp Trp Ile Arg Phe Asp Gln Ser Asn Ile Leu Cys Ser
 95                 100                 105

GTT TTT GGG ATC TCC ATG GTG TTC TCT GGC TTG TGC CCA CTT TTC CTG     384
Val Phe Gly Ile Ser Met Val Phe Ser Gly Leu Cys Pro Leu Phe Leu
110                 115                 120                 125

GGC AGT ACG ATG GCC ATT GAG AGG TGC ATC GGG GTC ACC AAC CCT CTA     432
Gly Ser Thr Met Ala Ile Glu Arg Cys Ile Gly Val Thr Asn Pro Leu
                130                 135                 140

TTC CAC TCT ACA AAG ATC ACG TCT AAG CAT GTG AAA ATG ATA CTG AGC     480
Phe His Ser Thr Lys Ile Thr Ser Lys His Val Lys Met Ile Leu Ser
                145                 150                 155

GGT GTG TGC ATG TTT GCT GTC TTC GTG GCC CTG TTG CCC ATC CTT GGA     528
Gly Val Cys Met Phe Ala Val Phe Val Ala Leu Leu Pro Ile Leu Gly
            160                 165                 170

CAC CGA GAT TAT CAA ATC CAA GCA TCC AGA ACT TGG TGC TTC TAC AAC     576
His Arg Asp Tyr Gln Ile Gln Ala Ser Arg Thr Trp Cys Phe Tyr Asn
175                 180                 185

ACA GAG CAC ATC GAA GAC TGG GAA GAC AGG TTC TAT CTC TTG TTC TTT     624
Thr Glu His Ile Glu Asp Trp Glu Asp Arg Phe Tyr Leu Leu Phe Phe
190                 195                 200                 205
```

```
TCT TCC CTG GGA CTC TTA GCT CTT GGC ATC TCA TTC TCG TGC AAC GCC      672
Ser Ser Leu Gly Leu Leu Ala Leu Gly Ile Ser Phe Ser Cys Asn Ala
                    210                 215                 220

GTC ACG GGA GTC ACA CTT TTG AGA GTG AAG TTT AGA AGT CAG CAG CAC      720
Val Thr Gly Val Thr Leu Leu Arg Val Lys Phe Arg Ser Gln Gln His
                225                 230                 235

AGG CAA GGC AGG TCT CAC CAC CTG GAG ATG GTC ATT CAG CTC CTG GCC      768
Arg Gln Gly Arg Ser His His Leu Glu Met Val Ile Gln Leu Leu Ala
            240                 245                 250

ATA ATG TGT GTC TCC TGC GTC TGC TGG AGT CCC TTT CTG GTG ACG ATG      816
Ile Met Cys Val Ser Cys Val Cys Trp Ser Pro Phe Leu Val Thr Met
255                 260                 265

GCC AAC ATT GCA ATC AAT GGA AAT AAT TCC CCA GTG ACC TGT GAG ACG      864
Ala Asn Ile Ala Ile Asn Gly Asn Asn Ser Pro Val Thr Cys Glu Thr
270                 275                 280                 285

ACG CTC TTT GCT CTC CGA ATG GCA ACC TGG AAC CAG ATA TTA GAC CCC      912
Thr Leu Phe Ala Leu Arg Met Ala Thr Trp Asn Gln Ile Leu Asp Pro
                290                 295                 300

TGG GTC TAC ATT CTG CTA CGG AAG GCT GTC CTT AGG AAC CTG TAC AAG      960
Trp Val Tyr Ile Leu Leu Arg Lys Ala Val Leu Arg Asn Leu Tyr Lys
                305                 310                 315

CTT GCC AGT CGC TGC TGT GGA GTG AAC ATC ATC AGC TTG CAC ATC TGG     1008
Leu Ala Ser Arg Cys Cys Gly Val Asn Ile Ile Ser Leu His Ile Trp
                320                 325                 330

GAA CTC AGC TCC ATC AAG AAT TCC TTA AAG GTT GCT GCT ATC TCT GAG     1056
Glu Leu Ser Ser Ile Lys Asn Ser Leu Lys Val Ala Ala Ile Ser Glu
            335                 340                 345

TCA CCG GCT GCA GAG AAG GAG AAT CAG CAA GCA TCT AGT GAG GCT GGA     1104
Ser Pro Ala Ala Glu Lys Glu Asn Gln Gln Ala Ser Ser Glu Ala Gly
350                 355                 360                 365

CTG TAAGTCAATG CA                                                   1119
Leu
```

(2) INFORMATION FOR SEQ ID NO:2:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Thr Thr Met Ser Ile Asn Ser Ser Lys Gln Pro Ala Ser Ser Ala
 -3          1               5                  10

Ala Gly Leu Ile Ala Asn Thr Thr Cys Gln Thr Glu Asn Arg Leu Ser
     15                  20                  25

Val Phe Phe Ser Ile Ile Phe Met Thr Val Gly Ile Val Ser Asn Ser
 30              35                  40                      45

Leu Ala Ile Ala Ile Leu Met Lys Ala Tyr Gln Arg Phe Arg Arg Lys
                 50                  55                      60

Ser Lys Ala Ser Phe Leu Leu Leu Ala Ser Gly Leu Val Ile Thr Asp
             65                  70                  75

Phe Phe Gly His Leu Ile Asn Gly Gly Ile Ala Val Phe Val Tyr Ala
             80                  85                  90

Ser Asp Lys Asp Trp Ile Arg Phe Asp Gln Ser Asn Ile Leu Cys Ser
         95                 100                 105

Val Phe Gly Ile Ser Met Val Phe Ser Gly Leu Cys Pro Leu Phe Leu
110                 115                 120                 125
```

```
Gly Ser Thr Met Ala Ile Glu Arg Cys Ile Gly Val Thr Asn Pro Leu
                130                 135                 140

Phe His Ser Thr Lys Ile Thr Ser Lys His Val Lys Met Ile Leu Ser
            145                 150                 155

Gly Val Cys Met Phe Ala Val Phe Val Ala Leu Leu Pro Ile Leu Gly
            160                 165                 170

His Arg Asp Tyr Gln Ile Gln Ala Ser Arg Thr Trp Cys Phe Tyr Asn
        175                 180                 185

Thr Glu His Ile Glu Asp Trp Glu Asp Arg Phe Tyr Leu Leu Phe Phe
190                 195                 200                 205

Ser Ser Leu Gly Leu Leu Ala Leu Gly Ile Ser Phe Ser Cys Asn Ala
                210                 215                 220

Val Thr Gly Val Thr Leu Leu Arg Val Lys Phe Arg Ser Gln Gln His
                225                 230                 235

Arg Gln Gly Arg Ser His His Leu Glu Met Val Ile Gln Leu Leu Ala
            240                 245                 250

Ile Met Cys Val Ser Cys Val Cys Trp Ser Pro Phe Leu Val Thr Met
    255                 260                 265

Ala Asn Ile Ala Ile Asn Gly Asn Asn Ser Pro Val Thr Cys Glu Thr
270                 275                 280                 285

Thr Leu Phe Ala Leu Arg Met Ala Thr Trp Asn Gln Ile Leu Asp Pro
                290                 295                 300

Trp Val Tyr Ile Leu Leu Arg Lys Ala Val Leu Arg Asn Leu Tyr Lys
                305                 310                 315

Leu Ala Ser Arg Cys Cys Gly Val Asn Ile Ile Ser Leu His Ile Trp
            320                 325                 330

Glu Leu Ser Ser Ile Lys Asn Ser Leu Lys Val Ala Ala Ile Ser Glu
    335                 340                 345

Ser Pro Ala Ala Glu Lys Glu Asn Gln Gln Ala Ser Ser Glu Ala Gly
350                 355                 360                 365

Leu (2) INFORMATION FOR SEQ ID NO:3:

(i) SEQUENCE CHARACTERISTICS:
        (A) LENGTH: 385 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

Met Ala Ser Met Trp Ala Pro Glu His Ser Ala Glu Xaa Ala His Ser
1               5                   10                  15

Asn Leu Ser Ser Thr Thr Asp Asp Cys Gly Ser Val Xaa Ser Val Ala
                20                  25                  30

Phe Pro Ile Thr Met Met Val Thr Gly Phe Val Gly Asn Ala Leu Ala
            35                  40                  45

Met Leu Leu Val Ser Arg Ser Tyr Arg Arg Arg Glu Ser Lys Arg Lys
50                  55                  60

Lys Ser Phe Leu Leu Cys Ile Gly Trp Leu Ala Leu Thr Asp Leu Val
65                  70                  75                  80

Gly Gln Leu Leu Thr Ser Pro Val Val Ile Leu Val Tyr Leu Ser Gln
                85                  90                  95
```

-continued

```
Arg Arg Trp Glu Gln Leu Asp Pro Ser Gly Arg Leu Cys Thr Phe Phe
            100                 105                 110

Gly Leu Thr Met Thr Val Phe Gly Leu Ser Ser Leu Val Ala Ser
            115                 120                 125

Ala Met Ala Val Glu Arg Ala Leu Ala Ile Arg Ala Pro His Trp Xaa
        130                 135                 140

Xaa Xaa Tyr Ala Ser His Met Lys Thr Arg Ala Thr Pro Val Leu Leu
145                 150                 155                 160

Gly Val Trp Leu Ser Val Leu Ala Phe Ala Leu Leu Pro Val Leu Gly
                165                 170                 175

Val Gly Arg Tyr Ser Val Gln Trp Pro Gly Thr Trp Cys Phe Ile Ser
            180                 185                 190

Thr Gly Pro Ala Gly Asn Glu Thr Asp Pro Ala Arg Glu Pro Gly Ser
        195                 200                 205

Val Ala Phe Ala Ser Ala Phe Ala Cys Leu Gly Leu Leu Ala Leu Val
        210                 215                 220

Val Thr Phe Ala Cys Asn Leu Ala Thr Ile Lys Ala Leu Val Ser Arg
225                 230                 235                 240

Xaa Cys Arg Ala Lys Ala Ala Val Ser Gln Ser Ser Ala Gln Trp Gly
                245                 250                 255

Arg Ile Thr Thr Glu Thr Ala Ile Gln Leu Met Gly Ile Met Cys Val
            260                 265                 270

Leu Ser Val Cys Trp Ser Pro Leu Leu Ile Met Met Leu Lys Met Ile
        275                 280                 285

Phe Asn Gln Met Ser Val Glu Gln Cys Lys Thr Gln Met Gly Lys Glu
        290                 295                 300

Lys Glu Cys Asn Ser Phe Leu Ile Ala Val Arg Leu Ala Ser Leu Asn
305                 310                 315                 320

Gln Ile Leu Asp Pro Trp Val Tyr Leu Leu Arg Lys Ile Leu Leu
                325                 330                 335

Arg Lys Phe Cys Xaa Xaa Xaa Xaa Xaa Xaa Xaa Xaa Xaa Xaa
            340                 345                 350

Xaa Xaa Gln Ile Arg Asp His Thr Asn Tyr Ala Ser Ser Thr Ser
        355                 360                 365

Leu Pro Cys Pro Gly Ser Ser Ala Leu Met Trp Ser Asp Gln Leu Glu
        370                 375                 380

Arg
385
```

(2) INFORMATION FOR SEQ ID NO:4:

(i) SEQUENCE CHARACTERISTICS:
        (A) LENGTH: 378 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:4:

```
Xaa Met Trp Pro Asn Gly Ser Xaa Xaa Ser Leu Gly Pro Cys Phe Arg
1               5                   10                  15

Pro Thr Asn Ile Thr Leu Glu Glu Arg Arg Leu Ile Ala Ser Pro Trp
            20                  25                  30

Phe Ala Ala Ser Phe Cys Val Val Gly Leu Ala Ser Asn Leu Leu Ala
        35                  40                  45
```

```
Leu Ser Val Leu Ala Xaa Gly Ala Arg Gln Gly Ser His Thr Arg
 50              55                  60

Ser Ser Phe Leu Thr Phe Leu Cys Gly Leu Val Leu Thr Asp Phe Leu
 65                  70                  75                  80

Gly Leu Leu Val Thr Gly Thr Ile Val Val Ser Gln His Ala Ala Leu
                 85                  90                  95

Phe Glu Trp His Ala Val Asp Pro Gly Cys Arg Leu Cys Arg Phe Met
            100                 105                 110

Gly Val Val Met Ile Phe Phe Gly Leu Ser Pro Leu Leu Gly Ala
            115                 120                 125

Ala Met Ala Ser Glu Arg Tyr Leu Gly Ile Thr Arg Pro Phe Ser Arg
        130                 135                 140

Pro Ala Val Ala Ser Gln Arg Arg Ala Trp Ala Thr Val Gly Leu Xaa
145                 150                 155                 160

Xaa Val Trp Ala Ala Ala Leu Ala Leu Gly Leu Leu Pro Leu Leu Gly
                165                 170                 175

Val Gly Arg Tyr Thr Val Gln Tyr Pro Gly Ser Trp Cys Phe Leu Thr
            180                 185                 190

Leu Gly Ala Xaa Xaa Xaa Xaa Xaa Xaa Xaa Xaa Glu Ser Gly Asp
        195                 200                 205

Val Ala Phe Gly Leu Leu Phe Ser Met Leu Gly Gly Leu Ser Val Gly
    210                 215                 220

Leu Ser Phe Leu Leu Asn Thr Val Ser Val Ala Thr Leu Cys His Val
225                 230                 235                 240

Xaa Tyr His Gly Gln Glu Ala Ala Gln Gln Arg Pro Arg Asp Ser Glu
                245                 250                 255

Xaa Xaa Xaa Val Glu Met Met Ala Gln Leu Leu Gly Ile Met Val Val
            260                 265                 270

Ala Ser Val Cys Trp Leu Pro Leu Leu Val Phe Ile Ala Gln Thr Val
        275                 280                 285

Leu Arg Asn Pro Pro Ala Met Ser Pro Ala Gly Gln Leu Ser Arg Thr
    290                 295                 300

Thr Glu Xaa Lys Glu Leu Leu Ile Tyr Leu Arg Val Ala Thr Trp Asn
305                 310                 315                 320

Gln Ile Leu Asp Pro Trp Val Tyr Ile Leu Phe Arg Arg Ala Val Leu
                325                 330                 335

Arg Arg Leu Xaa Xaa Xaa Xaa Xaa Xaa Xaa Xaa Xaa Xaa Xaa
            340                 345                 350

Xaa Xaa Gln Pro Arg Leu Ser Thr Arg Pro Arg Ser Leu Ser Leu Gln
        355                 360                 365

Pro Gln Leu Thr Gln Arg Ser Gly Leu Gln
    370                 375

(2) INFORMATION FOR SEQ ID NO:5:

(i) SEQUENCE CHARACTERISTICS:
        (A) LENGTH: 390 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

Xaa Met Ser Ile Asn Ser Ser Lys Gln Pro Ala Ser Ser Ala Ala Gly
1               5                  10                  15
```

-continued

```
Leu Ile Ala Asn Thr Thr Cys Gln Thr Glu Asn Arg Leu Ser Val Phe
             20                  25                  30

Phe Ser Ile Ile Phe Met Thr Val Gly Ile Val Ser Asn Ser Leu Ala
         35                  40                  45

Ile Ala Ile Leu Met Lys Ala Tyr Gln Arg Phe Arg Arg Lys Ser Lys
 50                  55                  60

Ala Ser Phe Leu Leu Leu Ala Ser Gly Leu Val Ile Thr Asp Phe Phe
 65                  70                  75                  80

Gly His Leu Ile Asn Gly Gly Ile Ala Val Phe Val Tyr Ala Ser Asp
                 85                  90                  95

Lys Asp Trp Ile Arg Phe Asp Gln Ser Asn Ile Leu Cys Ser Val Phe
            100                 105                 110

Gly Ile Ser Met Val Phe Ser Gly Leu Cys Pro Leu Phe Leu Gly Ser
            115                 120                 125

Thr Met Ala Ile Glu Arg Cys Ile Gly Val Thr Asn Pro Leu Phe His
    130                 135                 140

Ser Thr Lys Ile Thr Ser Lys His Val Lys Xaa Xaa Met Ile Leu Ser
145                 150                 155                 160

Gly Val Cys Met Phe Ala Val Phe Val Ala Leu Leu Pro Ile Leu Gly
                165                 170                 175

His Arg Asp Tyr Gln Ile Gln Ala Ser Arg Thr Trp Cys Phe Tyr Asn
            180                 185                 190

Thr Glu His Ile Glu Xaa Xaa Xaa Xaa Xaa Xaa Asp Trp Glu Asp
        195                 200                 205

Arg Phe Tyr Leu Leu Phe Phe Ser Ser Leu Gly Leu Leu Ala Leu Gly
    210                 215                 220

Ile Ser Phe Ser Cys Asn Ala Val Thr Gly Val Thr Leu Leu Arg Val
225                 230                 235                 240

Lys Phe Arg Ser Gln Gln His Arg Gln Gly Arg Ser His His Xaa Xaa
                245                 250                 255

Xaa Xaa Xaa Leu Glu Met Val Ile Gln Leu Leu Ala Ile Met Cys Val
            260                 265                 270

Ser Cys Val Cys Trp Ser Pro Phe Leu Val Thr Met Ala Asn Ile Ala
    275                 280                 285

Ile Asn Gly Asn Xaa Xaa Xaa Xaa Xaa Xaa Xaa Asn Ser Pro Val
290                 295                 300

Thr Xaa Cys Glu Thr Thr Leu Phe Ala Leu Arg Met Ala Thr Trp Asn
305                 310                 315                 320

Gln Ile Leu Asp Pro Trp Val Tyr Ile Leu Leu Arg Lys Ala Val Leu
                325                 330                 335

Arg Asn Leu Tyr Lys Leu Ala Ser Arg Cys Cys Gly Val Asn Ile Ile
            340                 345                 350

Ser Leu His Ile Trp Glu Leu Ser Ser Ile Lys Asn Ser Leu Lys Val
        355                 360                 365

Ala Ala Ile Ser Glu Ser Pro Ala Ala Glu Lys Glu Asn Gln Gln Ala
    370                 375                 380

Ser Ser Glu Ala Gly Leu
385                 390

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
```

```
        (D) TOPOLOGY: linear (ii) MOLECULE TYPE: cDNA (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 4
        (D) OTHER INFORMATION: /mod_base= i (ix) FEATURE:
        (A) NAME/KEY: modified_base
        (B) LOCATION: 8
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 16
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 19
        (D) OTHER INFORMATION: /mod_base= i (xi) SEQUENCE DESCRIPTION: SEQ ID NO:6:

ATNNYSWNYY TGGCNNTNNC CGAT                                              24

(2) INFORMATION FOR SEQ ID NO:7:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: cDNA (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO:7:

CKRAANAGNA TRTANACCCA NGGGTC                                            26
```

-continued (2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
CCAGCTTCTG GGTATAATGT GTGT                                                    24
```

(2) INFORMATION FOR SEQ ID NO:9:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
AGCAGSATAT ARGCCCAGGG GTCCAAGATC TGGTTCCRGG WTGCCATKCG                        50
```